United States Patent [19]
Lawhite et al.

[11] Patent Number: 4,753,270
[45] Date of Patent: Jun. 28, 1988

[54] CAM ACTUATOR ASSEMBLY FOR A PROGRAMMABLE INFUSION SYSTEM

[75] Inventors: Eric Lawhite, South Royalton, Vt.; David B. Vafiades, Lexington; Arthur J. Loud, Arlington, both of Mass.

[73] Assignee: Omni-Flow, Inc., Wilmington, Del.

[21] Appl. No.: 782,559

[22] Filed: Oct. 1, 1985

[51] Int. Cl.$^4$ .............................................. A61M 5/00
[52] U.S. Cl. .................... 137/624.18; 74/567
[58] Field of Search ............ 74/567; 137/624.11, 137/624.18, 624.2

[56] References Cited

U.S. PATENT DOCUMENTS

| | | | |
|---|---|---|---|
| 2,610,147 | 9/1952 | Lindsay | 137/624.4 X |
| 2,906,332 | 9/1959 | Rosten | 137/624.2 |
| 3,274,838 | 9/1966 | Kelch | 74/567 X |
| 3,372,708 | 3/1968 | Hotchkin | 137/624.2 |
| 3,539,878 | 11/1970 | Bell | 137/624.18 X |
| 4,303,376 | 12/1981 | Siekmann | 417/360 |
| 4,498,352 | 2/1985 | Hedelin | 74/568 |

FOREIGN PATENT DOCUMENTS 0154191  2/1985  European Pat. Off. .

Primary Examiner—Alan Cohan
Attorney, Agent, or Firm—Weingarten, Schurgin, Gagnebin & Hayes

[57] ABSTRACT

A single stacked cam bearing surface is used to actuate several cam followers in such manner that the cam bearing surface can move past one or more cam followers without actuation thereof but can be caused to stop at and actuate any desired cam follower. A stacked disc cam bearing surface of the improved cam actuator assembly of the present invention includes rotatable cam sub-assembly discs each having a surface well. The plurality of cam followers that bear against the bearing surface are selectively actuated by a controlled positioning of the cam sub-assembly discs that radially aligns the wells of the bearing surface with a selected cam follower. During a controlled rotation of the cam assemblies through an angular position of an intermediate cam follower, the wells of the sub-assembly discs of the cam bearing surface are radially mis-aliged, and thereby fail to actuate the cam follower during rotation through an intermediate angular position. The wells are aligned at a cam follower to be activated by a back and forth motion of the discs with the wells positioned under the followers.

17 Claims, 2 Drawing Sheets

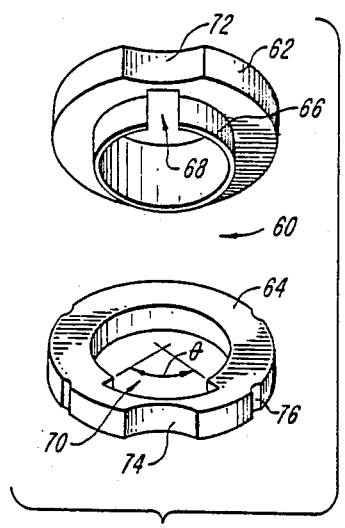
FIG. 2A
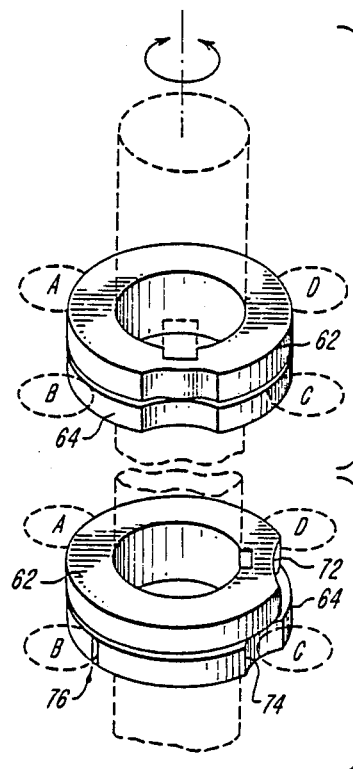
FIG. 2B
FIG. 2C
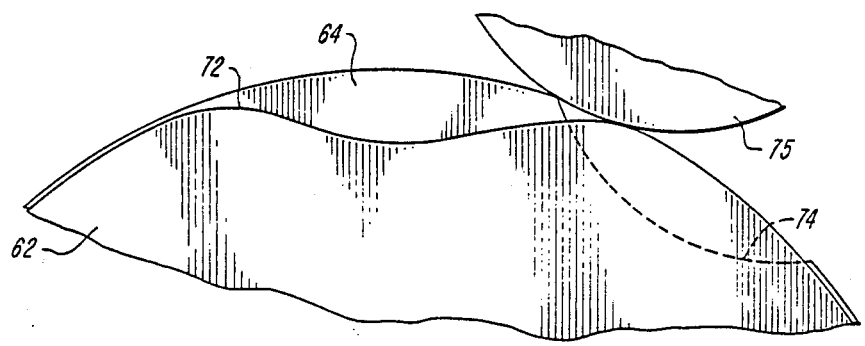
FIG. 3
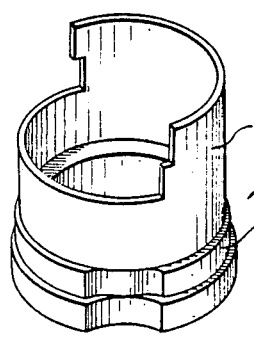
FIG. 4

CAM ACTUATOR ASSEMBLY FOR A PROGRAMMABLE INFUSION SYSTEM

FIELD OF THE INVENTION

This invention is directed to the field of electromechanical actuators, and more particularly, to an improved cam actuator assembly for a programmable infusion system.

BACKGROUND OF THE INVENTION

Epstein et al, commonly assigned co-pending U.S. utility patent application Ser. No. 578,180, filed Feb. 8, 1984, now abandoned, incorporated herein by reference, discloses an INFUSION SYSTEM HAVING PLURAL FLUID INPUT PORTS AND AT LEAST ONE FLUID OUTPUT PORT having a processor-controlled cam assembly for selectively controlling a plurality of input fluid valves and a patient output valve, among others. A processor is operative under program control to selectively actuate the plural fluid input port valves and the output patient valve in a selectable time sequence to administer infusates into the circulatory system of a patient undergoing infusion therapy. The plurality of fluid input port valves and the patient output port valve are integrally formed in a disposable fluid cassette, and the fluid cassette is itself further described and claimed in its ornamental design features in commonly owned co-pending U.S. design patent application Ser. No. 578,175, filed Feb. 8, 1984, now abandoned, incorporated herein by reference.

The processor controlled cam assembly includes a first singly-lobed cam mounted for rotation with the shaft of a processor-controlled stepper motor. A plurality of pivotable input valve rocker arms having rollers are spaced about the first cam with the rollers circumferentially disposed around the cam surface. A second doubly-lobed cam is mounted for rotation with the shaft of the stepping motor subjacent the first cam, and a pivotable patient output valve rocker arm is spaced with its roller adjacent the second cam. A plurality of plungers individually associated with an input or an output valve are mounted to corresponding rocker arms, and compression springs are mounted to respective plungers that are operative to so urge the plungers as to maintain the plural valves in a normally closed condition. The processor is operative to controllably rotate the stepper motor to bring the lobe of the first cam into abutting relation with a selected roller for actuating via its plunger the corresponding fluid input valve and is operative to bring either of the lobes of the second cam into abutting relation with its roller for actuating via its plunger the patient output valve.

The lobes of the several cams are so phased that it is not possible for an input valve to be simultaneously actuated with the patient output valve to prevent, among other things, accidental gravity flow infusion. A processor controlled solenoid having a ram in abutting relation with the output valve rocker arm is provided for actuating the patient output valve at the same time with an input valve such as during system priming, among others.

SUMMARY OF THE INVENTION

The improved cam actuator assembly for a programmable infusion system of the present invention includes a cam assembly having a master cam and a slave cam both mounted for rotation with the shaft of the processor controlled stepper motor. The master cam has a well, shaped to provide a constant torque, that is integrally formed with its peripheral surface. The slave cam has a well integrally formed with its peripheral surface. The master and slave cams are keyed to the shaft of the stepper motor in such a way that their peripheral surfaces together constitute the operative bearing surface of the cam assembly. The slave cam has a slot therethrough that cooperates with the keyed shaft to allow its well to lag the well of the master cam during controlled rotation. To actuate a selected input fluid valve plunger, the processor is operative to rotate the stepper motor to an angular position where the well of the master cam is angularly offset from the associated roller by that amount of angular lead that brings the well of the slave cam into alignment therewith. In a further operation, the processor is operative to rotate the shaft of the stepper motor in the reverse angular direction to bring its well into alignment with the well of the slave cam. Drag means are disclosed for prevention of the motion of the slave cam as the master cam is rotated in the reverse angular direction. The roller associated with the selected input valve therewith drops into the aligned wells, and the corresponding fluid input port valve is actuated.

A third output valve cam having diametrically opposed wells integrally formed on its peripheral surface is mounted for rotation with the shaft of the stepper motor, and in such a way that the wells of the several cams are so phased as to prevent simultaneous actuation of the input and output valves. The output port valve has an associated valve plunger connected to a compound-lever rocker arm, and a processor controlled solenoid having a ram abutting one of the lever arms of the compound-lever is provided to allow actuation of the output port valve and any one of the input port valves simultaneously. Means are disclosed coupled to the compound-lever rocker arm for providing a variable ram-contacting abutment surface.

The plungers associated with the several input port valves and of the output port valves are biased by a first coil spring operative to urge the associated plunger in a direction to hold the corresponding valve in a normally closed position, and are biased by a second coil spring operative to urge the associated plunger in a direction that allows the associated roller therefor to follow their corresponding cam actuators. The valves are all nominally in their closed condition.

The improved cam actuator assembly for a programmable infusion system of the present invention minimizes stepper motor torque requirements due, among other things, to the capability of the rollers to fall into the wells of the cam actuators provided therefor by action of spring force. In addition, due to the stability of the cooperative roller/well cam arrangement, the stepper motor may be turned-off during selected valve actuation, which conserves stepper motor power requirements, and which is particularly advantageous, among other things, during battery-powered operation.

A further advantage of the improved cam actuator assembly for a programmable infusion system of the present invention is its capability to actuate any selected input fluid valve from any other selected input fluid valve position without actuating an intermediate valve. The master and slave cams are mounted for relative rotation such that the compound bearing surface of the master/slave cam assembly passes through the angular position of an intermediate valve without thereby actuating the intermediate valve.

BRIEF DESCRIPTION OF THE DRAWINGS

These and other features and attendant advantages of the present invention will become apparent as the invention becomes better understood by referring to the following solely exemplary and non-limiting detailed description of a preferred embodiment thereof, and to the drawings, wherein:

FIG. 2 illustrates in FIG. 2A an exploded perspective view; in FIG. 2B a perspective view with the wells aligned; and in FIG. 2C a perspective view with the wells angularly offset; of the master and slave cams of the improved cam actuator assembly for a programmable infusion system according to the present invention;

FIG. 3 is a fragmentary schematic view illustrating the angular position of the well of the master cam relative to that of the well of the slave cam during controlled rotation of the improved cam actuator assembly for a programmable infusion system according to the present invention; and FIG. 4 is a perspective view illustrating an integral light interrupter formed with the master cam of the improved cam actuator assembly for a programmable infusion system according to the present invention.

DETAILED DESCRIPTION OF THE PREFERRED EMBODIMENT

Figure 1:
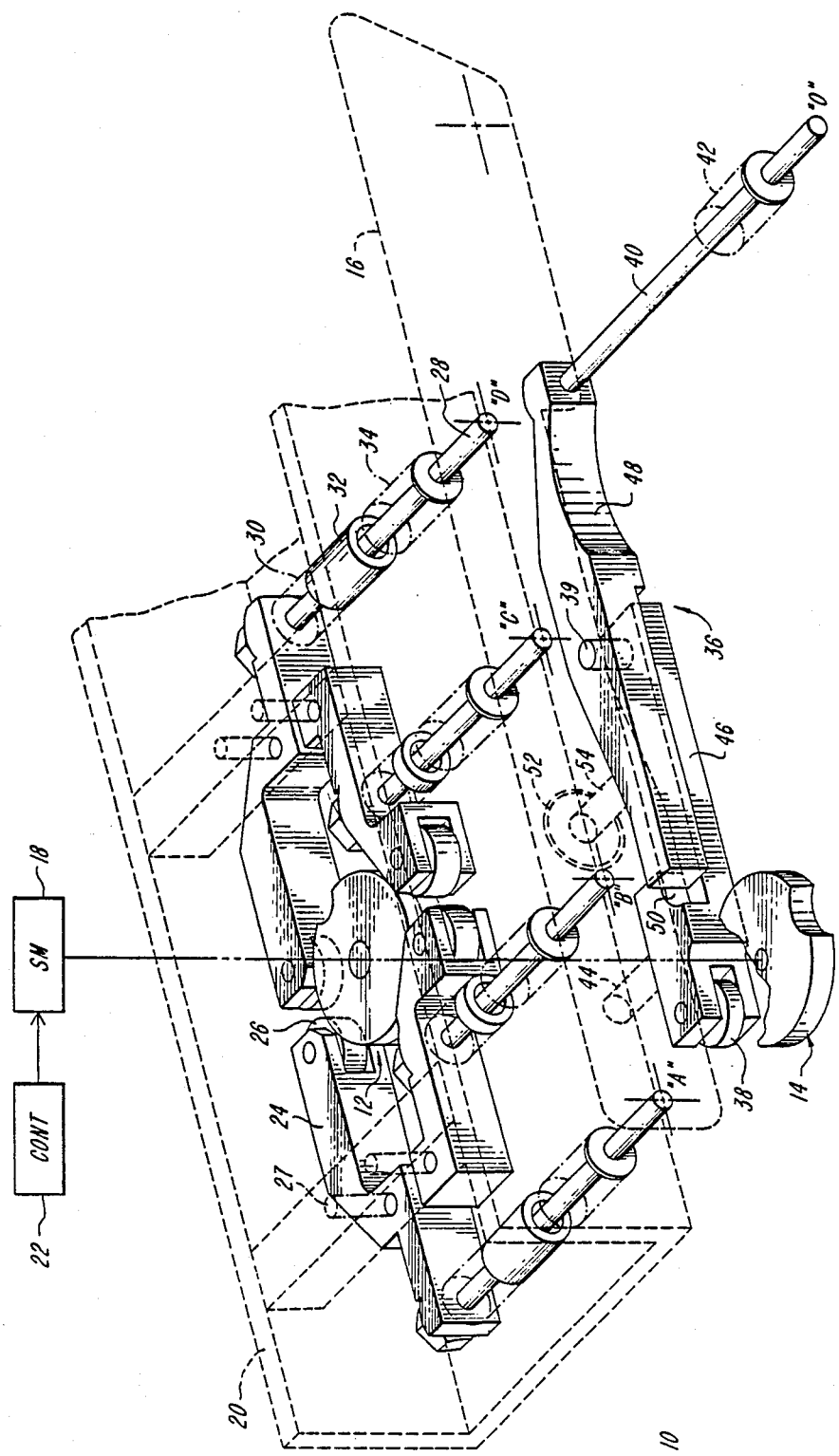
FIG. 1 is a perspective view illustrating the improved cam actuator assembly for a programmable infusion system according to the present invention.

Referring now to FIG. 1, generally designated at 10 is a fragmentary, partially exploded, perspective view illustrating the improved cam actuator assembly for a programmable infusion system according to the present invention. It should be noted that while in the preferred embodiment, relatively rotatable cams are disclosed, the principle of the present invention is not limited thereto, but can be advantageously employed with other cams including linear and x-y cams without departing from the inventive concept.

The assembly 10 includes a compound cam generally designated 12, to be described, selectively operable to control the state of a plurality of fluid input port valves designated "A", "B", "C", and "D", and a cam generally designated 14, to be described, selectively operable to control the state of a patient output valve designated "O". The valves "A"–"D" and the valve "O" are provided in a disposable fluid cassette schematically illustrated in dashed outline 16, that is more particularly disclosed in its functional aspect in the above-identified co-pending utility patent application and in its ornamental aspect in the above-identified design patent application. Each of the valves are formed as a resilient stop moveable between an open position that allows fluid communication and a closed position that prevents fluid communication therethrough. One or more infusates to be administered are coupled to fluid input ports, not shown, associated with the valves "A"–"D", and an intravenous line, not shown, is coupled to the patient output valve "O".

The cam actuator assembly 12 is operative to open any selected one of the plural fluid input valves "A'"–"D" to allow the corresponding infusate to be administered to flow through its fluid port into the fluid cassette 16, and the cam actuator assembly 14 is operative to open the patient output valve "O" to allow the selected infusate to flow from inside the cassette 16 and therethrough into the circulatory system of a patient undergoing infusion therapy.

The cam actuator assembly 12 includes a compound cam having a compound-bearing surface to be described. The compound cam 12 and the cam 14 are both mounted for rotation with the shaft of a stepper motor 18. The cam 14 is preferably mounted subjacent the cam 12. The stepper motor 18 is fastened to a U-shaped support member illustrated in dashed outline 20. A system controller 22 more fully disclosed in the above-identified co-pending utility patent application is operatively connected to the stepper motor 18 for controlling the angular orientation of its shaft, and therewith the angular orientation of the cams 12, 14. Since the system controller 22, as such, forms no part of the instant invention, it is not further described herein.

A plurality of rocker arms 24 having rollers 26 are mounted on pivots 27 to the U-shaped support 20 with the rollers 26 adjacent to, and in peripherally spaced relation around, the compound bearing surface of the compound cam 12. A like plurality of input port valve plungers 28 are slidably mounted in a corresponding one of the plurality of rocker arms 24 and fastened to an associated one of an enlarged head portion 25. The enlarged heads 25 and the confronting surfaces of the rocker arms 24 define gaps generally designated 29 therebetween operable in a manner to be described. Each of the input port valve plungers 28 are coaxially aligned with a corresponding one of the fluid input valves "A"–"D" and each extend through an aperture provided therefor in the U-shaped support member 20.

A compression spring schematically illustrated at 30 and an associated preload spacer 32 are slidably mounted on corresponding ones of the input port valve plungers 28 between and abutting a corresponding one of the rocker arms 24 and the confronting wall of the U-shaped support member 20. The compression springs 30 and associated spacers 32 are operative to apply a torque to their associated rocker arms 24 for urging the rollers 26 thereof into contact with the compound bearing surface of the compound cam 12. A compression spring schematically illustrated in dashed outline 34 is slidably mounted on and fastened between corresponding ones of the plurality of fluid valve input plungers 28 and the U-shaped support 20. The springs 34 are operative to apply a force to their associated plungers that urges the plungers into a corresponding one of the fluid input port valves "A"–"D" of the disposable cassette 16. The tension provided by the springs 30 and associated spacers 32 is selected to be greater than the tension provided by the springs 34.

A rocker arm generally designated 36 to be described having a roller 38 is mounted on a pivot 39 to the U-shaped support member 20 with its roller 38 adjacent the peripheral surface of the output valve cam actuator 14. An output valve plunger 40 is slidably mounted in and fastened to the end of the rocker arm 36 remote from the end thereof at which the roller 38 is mounted, with the output valve plunger 40 coaxially aligned with the output valve "O" of the disposable cassette 16. A compression spring schematically illustrated at 42 is slidably mounted on and fastened to the output valve plunger 40 that acts against the confronting wall of the U-shaped support member 20 for urging the plunger 40 into the output valve for closing it. A compression spring 44 is mounted between and abutting the rocker 36 and the U-shaped support 20. The force of the spring 44 and its perpendicular distance from the pivot 39 are selected to provide a moment larger than the moment provided by the force of the spring 42 and its perpendicular distance to the pivot 39 so that the roller 38 always is in abutting relation with the peripheral surface of the output valve cam 14.

The rocker arm 36 includes a first lever arm 46 to which the roller 38 is mounted, and a second compound lever arm 48 to which the plunger 40 is mounted. The lever arm 46 includes a shoulder 50. The lever arms 46, 48 have the common pivot 39, and the end of the lever arm 48 remote from the end to which the output valve plunger 40 is mounted abuts the shoulder 50 of the arm 46. A solenoid schematically illustrated in dashed outline 52 having a ram 54 is mounted to the U-shaped support member 20. A screw 55 is threaded through the arm 48 and in confronting relation to the ram 54. The screw 55 is selectively adjustable such that the ram 54 bears thereagainst only during the end portion of its travel.

Referring now to FIG. 2A, generally designated at 60 is an exploded perspective view illustrating the compound cam of the improved cam actuator assembly for a programmable infusion system according to the present invention. The compound cam 60 includes a master cam 62 and a slave cam 64. The master cam 62 has an integral annular bushing 66, and the slave cam 64 is journaled for relative angular rotation on the bushing 66 of the master cam 62. The bushing 66 is provided with a slot generally designated 68, and a key, not shown, fastened to the shaft of the stepper motor 18 (FIG. 1) is received in the slot 68. The master cam 62 is mounted for rotation with the shaft of the stepper motor 18 (FIG. 1) via the keyed slot 68. The slave cam 64 includes walls integrally formed on its inside circumferential wall defining a cutout generally designated 70 that subtends a preselected angle designated "θ" larger than the angle subtended by the key receiving slot 68 of the master cam 62. The cutout 70 allows the slave cam to lag the master cam during controlled rotation until the walls thereof gang the key, whereafter the master and slave cams rotate in unison. The cam 62 may be mounted for rotation with the shaft of the stepper motor by any other suitable means, such as by a radially projecting key integrally formed therewith that is received in a slot provided therefor in the shaft of the stepper motor.

The master cam 62 has a well 72 integrally formed with its outside peripheral surface, and the slave cam 64 has a well 74 integrally formed with its outside peripheral surface. The wells 72, 74 are symmetrically formed preferably about the radial center line of the key receiving slot 68 and of the cutout 70 respectively, although any other suitable angular orientation can also be provided. The surface defined by the well 72 of the master cam 62 is preferably shaped as a constant torque spiral as can best be seen in FIG. 3, and the surface of the well 74 of the slave cam 64 preferably has a shape that corresponds to the shape of the rollers 26 (FIG. 1). It should be noted that the wells 72, 74 can have any other suitable surface configuration.

The outside peripheral dimensions of the master cam 62 are selected to be slightly less than the outside peripheral dimensions of the slave cam 64. In the assembled condition of the cams 62, 64, the outside peripheral surface of the master cam 62 thus is always radially inwardly spaced from the outer peripheral surface of the slave cam 64. The differential in cam sizes during controlled rotation of the cams 62, 64 allows any input valve to be actuated without actuating an intermediate input valve as the stepper motor rotates through the position of the intermediate valve to the selected valve position.

The external peripheral surface of the slave cam 64 is provided with a plurality of radially-spaced surface detents generally designated 76. The detents 76 are spaced about the peripheral external surface of the slave cam 64 at angular positions corresponding to the angular positions at which corresponding ones of the rollers 26 (FIG. 1) are disposed around the compound cam 12 (FIG. 1), and at other angular positions. The detents 76 cooperate with the rollers 26 (FIG. 1) to retain the slave cam in an intended angular position during controlled rotation of the master cam. It should be noted that any other suitable drag providing means may also be employed.

The rollers 26 (FIG. 1) are positioned peripherally around the compound cam 12 such that each of the rollers 26 confronts and abuts the compound bearing surface of the master and slave cams 62, 64 (FIG. 2). For the angular position illustrated in FIG. 1, the rollers 26 bear on the compound bearing surface and pivot their associated rocker arms 24 about the pivots 27 in a counterclockwise direction through an angle sufficient to allow the gaps 29 to exist. The torque that is then applied to the rocker arms 24 (FIG. 1) is imparted by the springs 30 and spacers 32 alone, which therewith urges the rollers 26 (FIG. 1) against the external surface of the comparatively larger slave cam 64. For the angular position illustrated in FIG. 1, the input port valve plungers 28 are each displaced into its associated input port valve for holding it in a closed condition by action of the springs 34 alone, the gaps 25 decoupling the plungers from the springs 32.

To open any selected one of the fluid input port valves as exemplified for the "C" fluid input port in FIGS. 2B and 2C, the master cam 62 (FIG. 2B) is rotated to a preselected rotary position where its well 72 angularly leads the rotary position of the roller associated with the selected fluid input valve to be actuated. As the master cam 62 rotates to the phase lead angular position, an angular position is reached where the key attached to the shaft of the stepper motor gangs and drives the walls defining the cutout 70 (FIG. 2A) of the slave cam 64. With continued angular rotation to the phase lead position, the slave cam 64 rotates therewith to that angular position where its well 74 is radially-aligned with the roller of the associated valve to be actuated, as for the "C" valve illustrated in FIG. 2B. The rollers and detents are arranged so that when the well of the slave cam is radially-aligned with a roller of a selected valve to be actuated, the detents 76 are radially-aligned with the rollers of the valves that are to remain in the unactuated condition. The torque applied to the corresponding rocker arms urges the associated rollers against their associated, and now radially-aligned detents, and therewith imparts a frictional retaining force to the slave cam. The master cam 62 is then counter-rotated by that angle that brings the well 74 of the master cam 64 into radial alignment with the well 74 of the slave cam, not specifically shown. The torque produced by the springs 30 (FIG. 1) on the associated rocker arms thereby moves the roller associated with the valve to be actuated into the aligned wells and closes the corresponding gaps 29. Because the spring force of the springs 30 is greater than the spring force of the springs 32, the net differential torque moves the associated input fluid valve plunger out of its associated fluid valve, which opens the selected fluid port. It will readily be appreciated that the position of the rollers in the radially-aligned wells is dynamically stable, and that the stepper motor may thereby be turned off to conserve system power consumption.

To close the associated valve, the stepper motor is rotated in either angular direction, and the constant torque spiral defined by the well 72 of the master cam 62 bears against the associated roller, which readily follows the rise of the constant torque spiral. The associated rocker arm therewith pivots and the corresponding gap 29 forms. The spring force of the associated spring 34 then alone moves the associated plunger into the corresponding fluid valve for returning it to its nominal "closed" condition. In this way it has been found that the improved cam actuator assembly for a programmable infusion system of the present invention minimizes torque requirements to the stepper motor.

Any selected valve can be controllably actuated from any prior angular position of the cam 12 without therewith actuating a roller located at an angular position intermediate the prior angular position and the angular position of the valve selected to be actuated. For example, the cam assembly 12 (FIG. 1) is operable to actuate the valve "A" after having actuated the valve "C" by rotating either through the intermediate angular positions defined by the rollers associated with the valves "D" or "B". The angle "θ" subtended by the cutout 70 of the slave cam 62 is selected such that during controlled rotation of the cam 12 between selected stop locations of angular travel the wells 72, 74 of the master and slave cams 62, 64 are radially offset. The rollers 75 of the associated valves follow the compound cam bearing surface as can best be seen in FIG. 3, and the valve associated with the roller of an intermediate valve position remains in its normally closed state as the cam 12 rotates to the selected valve position.

Returning now to FIG. 1, the output valve actuator cam 14 has diametrically opposed constant torque spiral wells 80 formed along its peripheral cam surface. The wells 80 of the cam 14 and the wells 72, 74 (FIG. 2) of the compound cam assembly 12 preferably are so phased that it is impossible to have any selected one of the input valves "A"-"D" simultaneously open with the output valve "O". To open the output valve "O", the stepper motor 18 is rotated to bring either of the wells 80 in radially-aligned relation with the roller 38 on the rocker arm 36. In the radially-aligned condition, the roller 38 falls into the corresponding well 80 by action of the differential torque provided by the compression springs 42, 44 such that the lever arm 46 rotates about its pivot and draws the output valve plunger 40 out of the associated output valve placing it in the "open" condition. Whenever it is desirable to have any selected input valve simultaneously open with the patient output valve such as during priming, the solenoid 52 is actuated such that its ram 54 pivots the lever arm 48 for drawing the output valve plunger 40 out of the output valve and simultaneously the compound cam 12 is controllably rotated to actuate the selected fluid input valve.

Referring now to FIG. 4, generally designated at 82 is a perspective view illustrating another embodiment of the improved cam actuator assembly for a programmable infusion system. The assembly 82 is substantially identical with the assembly described above in connection with the description of FIGS. 2A-2C, except that a light interrupter 84 is integrally formed with the master cam 86. As disclosed in the above-identified co-pending utility patent application, the light interrupter 84 is operative in cooperation with light path providing means, not shown, to provide a signal indication of the rotary position of the stepper motor 18 (FIG. 1). It should be noted that the master cam with or without the integral light interrupter and the output cam are preferably formed of DELRIN, and the slave cam is preferably formed of NYLON, both trademarks of the Dupont Company, respectively for acetal and polyamide.

Many modifications of the presently disclosed invention will become apparent to those skilled in the art without departing from the scope of the appended claims.

What is claimed is:

1. A cam actuator assembly for a programmable infusion system having a disposable fluid cassette having a plurality of fluid input port valves and at least one patient output port valve, comprising:
   a support;
   a motor having a shaft and fastened to said support;
   a fluid input valve actuator assembly having a master cam having a circumferential surface and a first well formed in its circumferential surface mounted for rotation with the shaft of the motor, and a slave cam having a circumferential surface and a second well formed in its circumferential surface mounted to the master cam for relative angular rotation, the circumferential surface of the master cam being cooperative with the circumferential surface of the slave cam to provide a composite cam assembly bearing surface;
   a plurality of rocker arms having rollers pivotably mounted to the support with the rollers disposed circumferentially about the composite cam assembly bearing surface;
   a plurality of plungers slidably mounted in and fastened to corresponding ones of the rocker arms that are individually coaxially aligned with an associated one of the fluid input port valves; and
   means coupled to the support, the rocker arms, and to the plungers for imparting a torque to the rocker arms that urges the rollers into contact with the composite cam assembly bearing surface.

2. The invention of claim 1, wherein the motor is a stepper motor.

3. The invention of claim 1, wherein said master cam is mounted to the shaft of the motor by a key, and wherein said slave cam is mounted for relative angular rotation with respect to the master cam by a receiving key slot that subtends an angle larger than the angle subtended by the key for allowing the master cam to gang and drive the slave cam in such a way that as the shaft of the motor angularly rotates, the slave cam rotates in a predetermined phase relation thereto determined by the angle that the slot subtends.

4. The invention of claim 1, wherein said torque imparting means includes a plurality of first springs coupled between the rocker arms and the support operative to rotate the rocker arms in one angular direction, and a plurality of second springs coupled between the plungers and the support operative to rotate the rocker arms in the opposite angular direction.

5. The invention of claim 1, further including an output valve actuating cam having a peripheral surface and third and fourth wells integrally-formed in diametrically opposing relation in its peripheral surface; a rocker arm having a roller pivotally mounted to the support with its roller adjacent the peripheral surface of the output valve actuating cam; an output valve plunger slidably mounted in and fastened to the end of the rocker arm remote from the roller; and means for imparting a torque that operates to pivot the roller into contact with the patient output valve actuating cam.

6. The invention of claim 5, wherein said first, second, third, and fourth wells are so phased that for any angular position of the shaft of the motor an input valve plunger cannot be simultaneously actuated with the output valve plunger.

7. The invention of claim 6, wherein said rocker arm associated with said output valve cam is a compound lever having first and second lever arms mounted about a common pivot; and further including means coupled to one of the lever arms for actuating the output valve plunger.

8. The invention of claim 1, wherein said first well is a constant torque spiral.

9. The invention of claim 1, wherein said second well has a shape that corresponds to the shape of any one of said rollers.

10. The invention of claim 5, wherein said third and said fourth wells have a shape that corresponds to the shape of the roller on the arm associated therewith.

11. A method for actuating any one of a plurality of cam followers, comprising the steps of:
   abutting the cam followers against a compound-bearing surface defined by a compound cam that is constituted by a master cam having a well in its peripheral surface and a slave cam having a well in its peripheral surface;
   rotating the compound cam in a first angular direction such that the well of the master cam is in angularly spaced relation to, and the well of the slave cam is in radial alignment with, the angular position of a cam follower to be actuated; and
   rotating the master cam in a reverse angular direction to bring its well into radial alignment with the cam follower to allow the cam follower to fall into the coaxially-aligned wells of the master and slave cams for actuating the selected cam follower.

12. The invention of claim 11, further including the step of applying drag to the slave cam simultaneously with said rotation of said master cam in said reverse angular direction step.

13. An actuator assembly, comprising:

a compound cam assembly having an operative bearing surface, the compound cam including first and second constitutive master and slave cams each having an operative bearing surface including a well; the operative bearing surface of the compound cam being constituted by the operative bearing surfaces of the constitutive cams.

means for mounting the master and slave cams for movement relatively to each other in either of two directions so that when moved in a first direction aligned wells become not aligned and when moved in a second direction opposite the first direction the wells become aligned again;

a plurality of cam followers disposed about the compound cam in abutting relation with the compound cam bearing surface with at least one of the cam followers located at a position intermediate the location of at least two other cam followers; and means coupled to the compound cam for relatively moving the master and slave cams in such a way that the compound cam bearing surface actuates any selected cam follower when the wells are aligned with the selected cam follower, and for moving the master and slave cams in such a way that the compound cam bearing surface has misaligned wells as the compound cam moves through said intermediate position so that the cam follower at the intermediate position is not actuated as the master and slave cams move through the intermediate position.

14. The invention of claim 13, wherein said moving means includes a motor, wherein said master cam is mounted for rotation with said motor, and wherein said slave cam is mounted for angular rotation relative to said master cam and only in response to rotation of said master cam having rotated through a predetermined non-zero angle of rotation.

15. The invention of claim 14, wherein the external dimensions of said peripheral surface of said slave cam is larger than the external dimensions of said master cam, and further including means for applying drag to said slave cam.

16. The invention of claim 15, wherein said drag is applied to the peripheral surface of said slave cam.

17. The invention of claim 16, wherein said drag providing means includes a cam follower receiving detent integrally formed in the peripheral surface of the slave cam.

* * * * *